United States Patent [19]

Buchholz

[11] 4,102,931
[45] Jul. 25, 1978

[54] MANUFACTURE OF TERTIARY MERCAPTANS USING ZEOLITE CATALYSTS

[75] Inventor: Bernard Buchholz, Whitpain, Pa.

[73] Assignee: Pennwalt Corporation, Philadelphia, Pa.

[21] Appl. No.: 797,704

[22] Filed: May 17, 1977

[51] Int. Cl.$^2$ .......................................... C07C 148/00
[52] U.S. Cl. ................................................ 260/609 B
[58] Field of Search ..................................... 260/609 B

[56] References Cited

U.S. PATENT DOCUMENTS

| | | | |
|---|---|---|---|
| 2,435,545 | 2/1948 | Lyon | 260/609 B |
| 3,114,776 | 12/1963 | Warner | 260/609 B |
| 3,166,598 | 1/1965 | Cole | 260/609 B |
| 3,254,023 | 5/1966 | Miale et al. | 260/609 B |
| 3,408,403 | 10/1968 | Warner | 260/609 B |
| 3,534,106 | 10/1970 | Warner | 260/609 B |

*Primary Examiner*—Lewis Gotts
*Assistant Examiner*—Molly C. Eakin

[57] ABSTRACT

Certain synthetic zeolites have been found to provide high conversion over extended periods when used as catalysts in the addition reaction of hydrogen sulfide with branched, unsymmetrical olefins to produce tertiary mercaptans.

14 Claims, No Drawings

MANUFACTURE OF TERTIARY MERCAPTANS USING ZEOLITE CATALYSTS

This invention concerns the use of synthetic zeolite catalysts for the improved manufacture of tertiary mercaptans via Markownikoff addition of $H_2S$ to unsymmetrical, branched olefins as illustrated by the equation below,

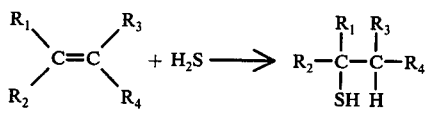

where $R_1$ and $R_2$ are alkyl, $R_3$ and $R_4$ are H or alkyl. Thus isobutylene + $H_2S$ yields tertiary butyl mercaptan, diisobutylene + $H_2S$ yields tertiary octyl mercaptan, propylene trimer + $H_2S$ yields tertiary nonyl mercaptan, and propylene tetramer + $H_2S$ yields tertiary dodecyl mercaptan. These tertiary mercaptans are well known articles of commerce being used in gas odorant blends, lubricant formulations, synthetic rubber manufacture, etc.

The use of conventional acid catalysts and clays to promote the Markownikoff addition of $H_2S$ to unsymmetrical, branched olefins is well known [Reid, Organic Chemistry of Bivalent Sulfur, Vol. I, p. 20 (1958)]. Among the numerous acid catalysts reported are: phosphoric acid on carbon or charcoal [U.S. Pat. No. 2,386,769 (1945), U.S. Pat. No. 2,386,770 (1945)], and [Ger. Pat. No. 708,261 (1941)], phosphoric acid on kieselguhr [U.S. Pat. No. 2,950,324 (1960)], nickel sulfide and acetic anhydride [Ger. Pat. No. 681,078 (1939)], nickel sulfide on pumice, silica, or Fuller's earth [U.S. Pat. No. 1,836,183 (1931)], sulfuric acid on carbon [U.S. Pat. No. 2,386,772 (1945)], red phosphorus on carbon [U.S. Pat. No. 2,386,771 (1945)], tungsten trioxide on carbon [U.S. Pat. No. 2,386,771 (1945)], boron trifluoride [Brit. 602,238 (1948), U.S. Pat. No. 2,434,510 (1948), U.S. Pat. No. 2,443,852 (1948)], silicotungstic acid [J. Applied Chem. 4, 285 (1954)], tin tetrachloride [U.S. Pat. No. 2,464,049 (1949)], aluminum chloride [U.S. Pat. No. 2,531,601 (1950)], alumina [Ind. and Eng. Chem. 40, 2308 (1948)], and silica-alumina [U.S. Pat. No. 2,392,554 (1946), U.S. Pat. No. 2,426,646 (1946), U.S. Pat. No. 2,392,555 (1946), U.S. Pat. No. 2,427,309 (1947), U.S. Pat. No. 2,435,545 (1948), U.S. Pat. No. 2,502,596 (1950), U.S. Pat. No. 2,610,981 (1952), U.S. Pat. No. 2,951,875 (1960), Ind. and Eng. Chem. 40, 2308 (1950)]. Commercially available silica-alumina catalysts containing about 12 to 26% alumina are currently preferred to manufacture $C_4$-$C_{12}$ tertiary mercaptans from olefins. These conventional catalysts are relatively non-homogeneous materials of amorphous or irregular crystal structure and non-uniform pore size.

It has now been found that excellent process results are obtained in the addition reaction of hydrogen sulfide with branched, unsymmetrical olefins (or oligomers thereof) of the type $R_1R_2C=CR_3R_4$, where $R_1$ and $R_2$ are the same or different alkyl radicals, and $R_3$ and $R_4$ are independently hydrogen or the same or different alkyl radicals, when said reaction is carried out in the presence of a synthetic zeolite catalyst having an alkali metal content (expressed as $Na_2O$) of less than 10 percent by weight.

The synthetic zeolite (molecular sieve) catalysts are synthetic aluminosilicates characterized by high uniformity, well-defined pore size, large surface area, complete crystallinity and excellent reproducibility. Their structures are described in the Union Carbide booklet F-08 entitled, "Linde Molecular Sieve Catalysts," and D. W. Breck's textbook, "Zeolite Molecular Sieves," John Wiley & Sons (1974). Various types are currently marketed by Linde (Union Carbide), Houdry (Air Products and Chemicals), Davison (W. R. Grace), Norton, and Akzo (Akzonia).

The basic structural units of synthetic zeolites are Si and Al atoms tetrahedrally coordinated with four oxygen atoms. The oxygen atoms are mutually shared between tetrahedral units contributing one of the two valence charges of each oxygen atom to each tetrahedron. Since aluminum atoms are trivalent, each $AlO_4^-$ is negatively charged. The charge on these units is balanced by cations, generally $Na+$ or $K+$, in the as-synthesized zeolites. These cations are exchangeable with other cations. For example, a divalent cation such as cobalt or nickelous nickel will replace 2 univalent cations; a trivalent cation such as chromium, lanthanum, or cerium will replace 3 univalent cations; and a tetravalent cation such as thorium will replace 4 univalent cations. It is thus possible to replace the alkali metal cations $Na+$ or $K+$ with catalytically more active cations such as $Ni+2$, $Co+2$, $Fe+2$ or $+3$, $Mo+2$ or $+3$, $Cr+3$, $La+3$, $Ce+3$, $Th+4$, etc., if desired.

Although many factors influence the catalytic activity of these zeolites, the three most important are:
1. The open framework structure with its attendant pore size.
2. The $SiO_2$:$Al_2O_3$ ratio of the framework.
3. The cations.

As in most commercial catalytic conversion processes, however, only the large-pore zeolites having pore openings in the range of 7 to 10 Angstroms are useful. The two most preferred are Type X and Type Y zeolites. The Type L, more siliceous than Type X and Type Y, also has a pore size in this range.

Type X has a chemical composition expressed in terms of oxide ratios of $Na_2O$:$Al_2O_3$:2-3 $SiO_2$ with a typical unit cell composition in the hydrated state of $Na_{86}[(AlO_2)_{86}(SiO_2)_{106}].264\ H_2O$. Type Y, on the other hand, has a composition of $Na_2O$:$Al_2O_3$:>3-6 $SiO_2$. When the $SiO_2$:$Al_2O_3$ molar ratio is 4.8, the hydrated unit cell composition is $Na_{56}[(AlO_2)_{56}(SiO_2)_{136}].264\ H_2O$. Both of these zeolites crystallize in the cubic system.

An important building block of these zeolites is the sodalite cage, a truncated octahedron unit consisting of 24 $(Si,AlO_4)$ units. In Type X and Type Y the sodalite cages are connected through 4 of the 8 hexagonal faces in a tetrahedral arrangement. The pores thus created are defined by a 12-member ring of oxygen atoms, approximately 7-9Å in size, opening into a central cavity of about 11Å in diameter.

The preferred synthetic zeolites are types X and Y because of their larger pore sizes. The ability of the Y type to withstand higher temperatures without losing its crystalline structure makes it the most preferred zeolite catalyst for this invention.

The zeolites, as prepared, generally contain as the cation about 13 percent sodium (as $Na_2O$) or equivalent amount of other alkali metal. As explained above, this cation may be replaced with other cations to reduce the sodium content. In this invention the zeolite catalyst contains less than 10 percent alkali metal (expressed as Na$_2$O), preferably less that 5 percent and most preferably less than 2.5 percent by weight.

In general, the unsymmetrical olefins used in the process of this invention are those of the type R$_1$R$_2$C=CR$_3$R$_4$ where R$_1$ and R$_2$ are the same or different alkyl radicals, and R$_3$ and R$_4$ are independently hydrogen or the same or different alkyl radicals. The term "olefins" includes oligomers preferably homo-oligomers of the above described types of compounds. The branched unsymmetrical olefin is preferably employed in the form of a propylene homopolymer, isobutylene homopolymer, or isobutylene monomer. Propylene polymers and a method for their preparation are disclosed in U.S. Pat. No. 2,951,875 at column 2 lines 48–69.

The addition reaction, as employed herein, is well known in the art. It is preferably carried out with a molar excess of H$_2$S at super atmospheric pressures and at temperatures ranging between 20° to 200° C. Most preferably, pressures ranging between 20 and 1000 p.s.i.g. and temperatures ranging between 50° and 150° C are used during the reaction carried out over the solid zeolite catalyst.

The process, especially when used commercially, is carried out continuously, although batch operation is contemplated. The catalyst is used in amounts based on the number of gram-moles of unsymmetrical olefin passed over the catalyst in a 24 hour period. Thus, the process is operated using from about 20 to about 250, preferably 25 to 150, gram moles of olefin per kilogram of zeolite catalyst in a 24 hour period.

The advantages of the synthetic zeolite catalysts over the conventional silica-alumina catalyst are illustrated by the examples below. The synthetic aluminosilicate zeolite catalyst used in examples 1-6 is Linde's 31-411 (⅛ inch extrudate), which is a type Y zeolite containing about 40% Al$_2$O$_3$ and 57% silica in which the sodium from the original sodium aluminosilicate has been exchanged for ammonium, followed by extruding and calcining, to remove most of the ammonia, and thereby obtaining a partially decationized zeolite catalyst. A conventional silica-alumina (alumina on silica) catalyst containing about 13% Al$_2$O$_3$ and 85% silica was used for comparative purposes. Commercial conventional silica-alumina catalysts are available from Davison (W. R. Grace), Akzo (Akzonia), Houdry (Air Products) and others.

Example 1 — Tertiary Dodecyl Mercaptan

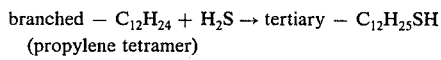
(propylene tetramer)

Propylene tetramer was pumped at a measured rate and H$_2$S was passed through a Drierite drying tube and metered as a gas through a flowmeter. The reactants were mixed just above and passed downward through the vertically mounted reactor. The reactor was a 316SS tubular, fixed bed type, heated externally with an electric furnace.

The reactor was equipped with a sliding vertical thermocouple probe going up the center of the catalyst bed. Temperatures recorded are the hot spot temperatures in the bed. Pressure was obtained from the H$_2$S cylinder and was maintained with a pressure control valve.

The crude product from a single pass over the catalyst was collected at atmospheric pressure in a glass receiver topped with a Vigreoux column and a condenser kept just cold enough to maintain a slight H$_2$S reflux, while allowing the bulk of the excess H$_2$S to flash off to an outside burner.

The crude t-dodecyl mercaptan was collected over one-hour run periods, weighed, and titrated for mercaptan content (as C$_{12}$H$_{25}$SH) to arrive at the % conversion.

Unless otherwise indicated, the following reaction conditions were employed in the laboratory to simulate a commercial t-dodecyl mercaptan manufacturing process:

1. Tetramer pumping rate (mole velocity): 27 g-moles/24 hour day/kg. catalyst.
2. H$_2$S/tetramer molar feed ratio: 10/1
3. Pressure: 135 psig.
4. Catalyst bed temperature: 85°–95° C The effectiveness of the conventional silica-alumina catalyst was determined to establish a performance base line. Conversions to t-dodecyl mercaptan at the standard (27) tetramer mole velocity and at twice (54) and treble (81) the standard throughput rates were determined.

Next the effectiveness of a zeolite (Linde 31-411) catalyst containing 2.29% by weight of sodium oxide was determined at the standard (27) tetramer mole velocity and at twice (54), treble (81) and quadruple (108) the standard throughput rate. The results are compared in Table 1 below.

TABLE 1

| Zeolite Catalyst Use period-cumulative hrs. | Tetrameter Mole Velocity (moles/day/kg. catalyst) | % Conversion to t-dodecyl mercaptan | |
|---|---|---|---|
| | | Silica-alumina Catalyst | Zeolite Catalyst |
| 63 | 27 | 85 | 97.7 |
| 84 | 54 | 74 | 97.8 |
| 91 | 78 | 71 | 94.1 |
| 102 | 108 | — | 90.8 |

These data show the zeolite catalyst to be significantly more active for adding H$_2$S to propylene tetramer than the conventional silica-alumina catalyst. At the lower pumping rates, the zeolite catalyst gives an almost quantitative conversion of the tetramer to t-dodecyl mercaptan in a single pass, eliminating the need to recycle unreacted tetramer in a commercial process. At pumping rates as high as 108 g-mols of tetramer/24-hour day/kg. catalyst, the zeolite catalyst gives 90% conversion, whereas the conventional silica-alumina catalyst gives much lower and less economical conversion.

Example 2 — Tertiary Dodecyl Mercaptan

A shortcoming of the conventional silica-alumina catalysts is that they are sensitive to moisture often present in the olefin and H$_2$S feeds, becoming gradually deactivated for the addition reaction. As a result of the formation of stable hydrates, these conventional catalysts must then be heated to 500° C to remove the hydrated water and completely restore their catalytic activity.

In this experiment, 40 cc. of water was intentionally pumped over a 200 g. charge of the zeolite (Linde 31-411) catalyst. Using the same equipment and procedure as in Example 1, it was shown that the zeolite catalyst is likewise deactivated by water, but a considerably milder heat treatment (240° C) is sufficient to completely restore its activity, so that near-quantitative, single pass conversions of propylene tetramer to t-dodecyl mercaptan are again obtained. The experiment was repeated a second time with the same results as shown in Table 2 below.

TABLE 2

| Catalyst Treatment | Catalyst Use cumulative hr. | % Conversion tetramer → mercaptan |
|---|---|---|
| Fresh catalyst, 27 mole vel. | 63 | 97.7 |
| Same catalyst, 54 mole vel. | 84 | 97.8 |
| Same catalyst, 78 mole vel. | 91 | 94.1 |
| Same catalyst, 108 mole vel. | 102 | 90.8 |
| Catalyst slugged with 40 cc. water | 106 | 20 |
| Continued operation, 27 mole vel. | 126 | 20→ 85 |
| Operation after 230° C heat treatment | 142 | 90.4 |
| Operation after 140° C heat treatment | 161 | 93.5 |
| Operation after 240° C heat treatment | 190 | 99.4 |
| Continued operation, 54 mole vel. | 204 | 94.0 |
| Catalyst slugged again, 40 cc. H$_2$O | 208 | 44 |
| Operation after 240° C heat treatment | 216 | 97 |
| Continued operation, 27 mole vel. | 231 | 99 |

Example 3 — Tertiary Dodecyl Mercaptan

Using the same equipment and procedure as in Example 1, the zeolite (Linde 31-411) catalyst was intentionally overheated during operation of the process to determine if any permanent deactivation of the catalyst results. Conversions to t-dodecyl mercaptan were lower during operation at the higher temperature, but returned to normal when the catalyst temperature was restored to the standard 90° C. The results are summarized in Table 3 below.

TABLE 3

| Catalyst Treatment | Catalyst Use cumulative hr. | % Conversion tetramer*→mercaptan |
|---|---|---|
| Operation at standard 90° C | 231 | 99 |
| Tert-nonyl mercaptan produced/26 hrs.** | 257 | 92–94 |
| Process operated at 130° C(40° C overheat) | 276 | 83 |
| Process operated at 110° C (20° overheat) | 288 | 91 |
| Operation at standard 90° C | 310 | 97 |

*propylene trimer was used to replace the tetramer feed for 26 hours of this run.
**see Example 6 following.

Example 4 — Tertiary Dodecyl Mercaptan

Using the same equipment and procedure as in Example 1, the effect of wet propylene tetramer on the zeolite catalyst was compared with the conventional silica-alumina catalyst.

The process was operated at standard conditions with the zeolite (Linde 31-411) catalyst for 48 hours using wet propylene tetramer. The gradual decrease in conversion due to loss in catalyst activity is shown in Table 4 below.

TABLE 4

| Propylene tetramer Feed Material | Catalyst Use cumulative hr. | % Conversion tetramer→mercaptan |
|---|---|---|
| Propylene tetramer - lab. dried. | 435 | 98.0 |
| same containing 24 ppm H$_2$O | 468 | 94.0 |
| same containing 60 ppm H$_2$O | 483 | 92.9 |

The zeolite catalyst was dropped after 483 hours and replaced with fresh conventional silica-alumina catalyst. Using standard operating conditions the conversion to t-dodecyl mercaptan decreased gradually from an initial 87% (with dried propylene tetramer) to 82% after operating for 46 hours with wet (60 ppm H$_2$O) tetramer.

Example 5 — Tertiary Octyl Mercaptan branched — $C_8H_{16}$ + $H_2S$ → tert — $C_8H_{17}SH$
(diisobutylene)

Diisobutylene (DIB) and H$_2$S were reacted over the zeolite (Linde 31-411) catalyst at DIB mole velocity 27 g. moles/day/kg. catalyst, 90° C catalyst bed temperature, 135 psig pressure and 10/1 molar ratio of H$_2$S/DIB. The average single-pass conversion of DIB to tert-C$_8$H$_{17}$SH over 48 hours of operation was 95.8%.

Example 6 — Tertiary Nonyl Mercaptan branched — $C_9H_{18}$ + $H_2S$ → tert — $C_9H_{19}SH$
(propylene trimer)

Propylene trimer was reacted with H$_2$S over the zeolite (Linde 31-411) catalyst at a trimer mole velocity of 27 g. moles/day/kg. catalyst, 90° C catalyst temperature, 10/1 molar ratio of H$_2$S/trimer, and 135 psig pressure for a total of 26 hours. Single pass conversions in the range 92–94% were obtained.

Example 7 — Tertiary Dodecyl Mercaptan

A zeolite catalyst (Linde's 30-411), which is synthetic sodium aluminosilicate, type Y, containing about 13% Na$_2$O, 64% SiO$_2$ and 23% Al$_2$O$_3$, was tried and found to have relatively low activity for the addition of H$_2$S to propylene tetramer. The best result obtained was a 70% conversion of tetramer to tert-dodecyl mercaptan.

Example 8 — Tertiary Dodecyl Mercaptan

A zeolite catalyst (Linde's 33-411), which is a more highly refined version of the zeolite of Examples 1-6, in which the Na$_2$O level has been reduced to 0.12 wt. %, was found to be highly effective for adding H$_2$S to propylene tetramer as shown in Table 5 below.

TABLE 5

| Catalyst Treatment | Catalyst Use cumulative hr. | % Conversion tetramer→ mercaptan |
|---|---|---|
| Fresh zeolite catalyst | 16 | 97.5 |
| Same zeolite catalyst | 26 | 99+ |
| Catalyst slugged with 40 cc. $H_2O$ | 33 | 60 |
| Operation after 140° C heat treatment | 50 | 60→ 90.5 |
| Operation after 240° C heat treatment | 63 | 90.5→ 97.5 |
| Continued operation | 70 | 97.6 |
| Continued operation | 78 | 98.4 |

Example 9 — Tertiary Dodecyl Mercaptan

A type X, rare earth stabilized synthetic zeolite (Davison's "Crex") was screened using the same equipment and procedure described in Example 1. Conversions of propylene tetramer to t-dodecyl mercaptan were high (87%) over the first ten hours of operation, but declined over the next 50 hours (to 55%).

I claim:

1. A method for preparing tertiary mercaptans having from 4 to 18 carbon atoms comprising reacting hydrogen sulfide with a branched, unsymmetrical olefin or oligomer thereof, said olefin having the formula $R_1R_2C=CR_3R_4$ where $R_1$ and $R_2$ are the same or different alkyl radicals, and $R_3$ and $R_4$ are independently either hydrogen or the same or different alkyl radicals, in the presence of a catalytic amount of a synthetic zeolite of the X or Y type having an alkali metal content, expressed as $Na_2O$, of less than 10 percent by weight.

2. The method of claim 1 wherein a molar excess of hydrogen sulfide and the olefin are continuously passed over said zeolite at a rate of from about 20 to about 250 gram-moles of olefin per day for each kilogram of zeolite.

3. The method of claim 2 wherein the reaction is carried out at superatmospheric pressure and temperatures ranging from about 20° to about 200° C.

4. The method of claim 3 wherein the reaction pressure ranges from about 20 to 1000 psig and the temperatures range from 50° – 150° C.

5. The method of claim 3 wherein the alkali metal content has been reduced to below 10 percent by exchanging the alkali metal ions with protons or catalytically active cations.

6. The method of claim 3 wherein the alkali metal content has been reduced to below 10 percent by exchanging the alkali metal ions with ammonium ions and thereafter the zeolite is calcined to remove at least a major proportion of the ammonia.

7. The process of claim 3 wherein the alkali metal content is below 5 percent.

8. The process of claim 6 wherein the catalyst is a Y type zeolite.

9. The process of claim 8 wherein the alkali metal content has been reduced to below 5 percent by exchanging sodium ions with ammonium ions, and thereafter the zeolite is calcined to remove at least a major proportion of the ammonia.

10. The process of claim 8 wherein the alkali metal content is below 2.5 percent.

11. The process of claim 9 wherein the olefin is isobutylene.

12. The process of claim 9 wherein the olefin is diisobutylene.

13. The process of claim 9 wherein the olefin is propylene trimer.

14. The process of claim 9 wherein the olefin is propylene tetramer.

* * * * *